United States Patent [19]

Bryndza

[11] Patent Number: 4,810,815

[45] Date of Patent: Mar. 7, 1989

[54] ACCELERATION OF DIENE HYDROCYANATION

[75] Inventor: Henry E. Bryndza, Wilmington, Del.

[73] Assignee: E. I. Du Pont De Nemours and Company, Wilmington, Del.

[21] Appl. No.: 116,658

[22] Filed: Nov. 4, 1987

[51] Int. Cl.[4] .................................... C07C 120/02
[52] U.S. Cl. .................................... 558/338; 558/335; 558/337; 558/339; 558/340; 558/341
[58] Field of Search .............................. 558/338, 335

[56] References Cited

U.S. PATENT DOCUMENTS

| 2,571,099 | 10/1951 | Arthur, Jr. et al. | 260/465.3 |
| 3,496,215 | 2/1970 | Drinkard, Jr. et al. | 260/465.8 |
| 3,496,217 | 2/1970 | Drinkard, Jr. et al. | 260/465.8 |
| 3,766,237 | 10/1973 | Chia et al. | 260/465.3 |
| 3,778,462 | 12/1973 | Taylor et al. | 260/465.3 |
| 3,903,120 | 9/1975 | Shook, Jr. et al. | 260/439 R |
| 4,082,811 | 4/1978 | Shook, Jr. et al. | 260/465.8 R |
| 4,151,194 | 4/1979 | Wu et al. | 260/464 |

OTHER PUBLICATIONS

Taylor et al., J. of Catalysis 26, pp. 254–260 (1972).
Wu et al., Symposium on Homogeneous Catalysis (1980), pp. 372–381.
Tolman et al., Advances in Catalysis, vol. 33, Acad. Press (1985) pp. 1–46.

Primary Examiner—Joseph Paul Brust

[57] ABSTRACT

Process of polyene hydrocyanation, in particular diene hydrocyanation, wherein a promotionally effective amount of any acid with a $pK_a$ above about 2 and below and 14, preferably aryl alcohols such as phenol and cresols, is used.

6 Claims, 2 Drawing Sheets

Cyclohexadiene Semi-Batch Hydrocyanations

ACCELERATION OF DIENE HYDROCYANATION

BACKGROUND OF THE INVENTION

1. Field of the Invention

This invention relates to the process of polyene hydrocyanation using promoters and, in particular, to hydrocyanation of dienes by hydrogen cyanide, a nickel catalyst, and a promotionally effective amount of an aryl alcohol.

2. Summary of the Background

It is known that the addition of hydrogen cyanide to double bonds adjacent to an activating group, such as a nitrile or carbonyl group, proceeds with relative ease. The addition of hydrogen cyanide to unactivated double bonds, however, proceeds only with difficulty, if at all, and normally requires the use of high pressures of about 1000 psi (7 MPa) or more and high temperatures in the range of 200° to 400° C.

Arthur, et al., U.S. Pat. No. 2,571,099, disclose an improved hydrocyanation process that involves the use of nickel carbonyl, Ni(CO)$_4$, with or without the addition of a tertiary aryl phosphine or arsine. This process produces a relatively high percentage of undesirable polymeric products when applied to monoene starting materials and a relatively poor yield in all cases. Furthermore, this process is not satisfactory for the production of adiponitrile (ADN) from 3 or 4-pentenenitrile (3PN or 4PN).

Drinkard, et al., U.S. Pat. No. 3,496,215, disclose a process for hydrocyanating olefinically unsaturated organic compounds with zerovalent nickel phosphite catalysts of the general formula, Ni(PXYZ)$_4$, wherein X is OR and Y and Z are selected from the class consisting of OR and R, wherein R is selected from the class consisting of alkyl and aryl groups having up to 18 carbon atoms.

Drinkard, et al., U.S. Pat. No. 3,496,217, disclose an improvement in monoene hydrocyanation using a nickel catalyst and a metal cation promoter selected from the class consisting of zinc, cadmium, beryllium aluminum, gallium, indium, silver, titanium, zirconium, hafnium, germanium, tin, vanadium, niobium, scandium, chromium, molybdenum, tungsten, manganese, rhenium, palladium, thorium, erbium, iron, and cobalt.

Chia, et al., U.S. Pat. No. 3,766,237, disclose an improved process for the hydrocyanation of selected unsaturated organic compounds utilizing a nickel complex catalyst, preferably of the general structure

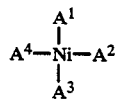

wherein A$^1$, A$^2$, A$^3$, and A$^4$ are neutral ligands that may be the same or different and are selected from the class consisting of M(XYZ) wherein M is selected from the class consisting of P, As, and Sb, and wherein X, Y, and Z may be the same or different and are selected from the class consisting of R and OR, and wherein R is selected from the class consisting of alkyl and aryl groups having up to 18 carbon atoms, in the presence of an excess of a triaryl phosphite having the formula, P(OAr)$_3$, wherein Ar is selected from the class of aryl groups of up to 18 carbon atoms. Use of a promoter is not necessary in this process; however boron compounds or cationic forms of a metal selected from the class consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron, and cobalt can be used.

Shook, et al., U.S. Pat. No. 3,903,120, disclose an improved process or the synthesis of zerovalent complexes of nickel of the types, Ni(MZ$_3$)$_4$ and Ni(MZ$_3$)$_2$A, with a ligand such as MZ$_3$ wherein M is P, As, or Sb, Z is R or OR, and R is an alkyl or aryl group having up to 18 carbon atoms and the R's of a given ligand may be the same or different, and at least one Z is OR, and A is a monoene having 2 to 20 carbon atoms.

Shook, U.S. Pat. No. 4,082,811, discloses a process for the recovery of catalyst components from a catalyst residue obtained from the hydrocyanation of olefins using a catalyst comprising zerovalent nickel complex promoted with a triarylborane and comprising nickel cyanide, triarylborane, and complexes of the foregoing. Additionally, a recent description of the hydrocyanation process can be found therein.

Taylor, et al., U.S. Pat. No. 3,778,462, and Wu, et al., U.S. Pat. No. 4,151,194, disclose a process for hydrocyanations of monoenes wherein the hydrocyanation reaction is carried out in the presence of a zerovalent nickel catalyst, a promoting amount of a cation of a metal constituting the required Lewis acid, and using a solvent that is an aryl compound containing from 6 to 20 carbon atoms per molecule and containing at least one hydroxyl group directly connected to a ring carbon atom that includes phenol and cresols.

Taylor, et al., J. Cat. 26, 254–260 (1972), report monoene hydrocyanations run in cresol solvents in the necessary presence of a Lewis acid and that, in these Lewis acid-promoted reactions, cresol solvents show increased rates over reactions run in toluene or acetonitrile solvents.

Wu, et al., Symposium on Homogeneous Catalysis, Am. Chem. Soc. 372–381 (1980), report that, in contrast to monoene hydrocyanation, phenol and cresol solvents do not lead to rate enhancement in diene hydrocyanation.

A general summary of nickel-catalyzed olefin hydrocyanation is found in Tolman, et al., Adv. Cat. 33, 1–46 (1985).

None of these references discloses or suggests the instant process of polyene hydrocyanation using a promotionally effective amount of any acid with a pK$_a$ above about 2 and below about 14, preferably from about 6 to about 12, in the presence or absence of a solvent.

SUMMARY OF THE INVENTION

This invention is an improved hydrocyanation process wherein a reactor is fed with a polyene that is preferably a diene, hydrogen cyanide, a zerovalent nickel catalyst, and a promotionally effective amount of any acid with a pK$_a$ above about 2 and below about 14, preferably from about 6 to about 12, in the presence or absence of a solvent. A preferred promoter is an aryl alcohol of the structure

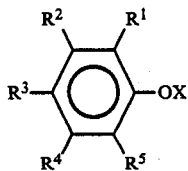

wherein

X is any isotope of hydrogen, and

R$^1$, R$^2$, R$^3$, R$^4$, and R$^5$ are selected from the group consisting of hydrogen, hydrocarbyls, and hydrocarbyls containing groups selected from the group consisting of

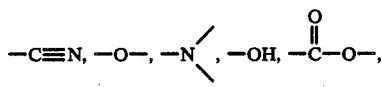

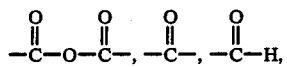

halides, and fluorocarbyls. Phenol and cresols are preferred aryl alcohols, and a preferred embodiment uses less than about 5 M aryl alcohol.

A preferred polyene for this improved hydrocyanation process is one selected from the group consisting of butadiene; 1,3-hexadiene; 1,4-hexadiene; 1,5-hexadiene; 1,3-cyclooctadiene; 1,4-cylcooctadiene; 1,5-cylcooctadiene; 1,5,9-cyclododecatriene; cyclopentadiene; dicyclopentadiene; norbornadiene; divinylbenzenes; diisopropenylbenzenes; and divinylcyclobutanes.

The instant process increases the rate of polyene hydrocyanation, improves catalyst lifetime, accelerates diene hydrocyanation rates, and lowers the amount of catalyst required for diene hydrocyanation due to the increased efficiency of the existing catalyst.

DETAILED DESCRIPTION OF THE INVENTION

Figure 1:
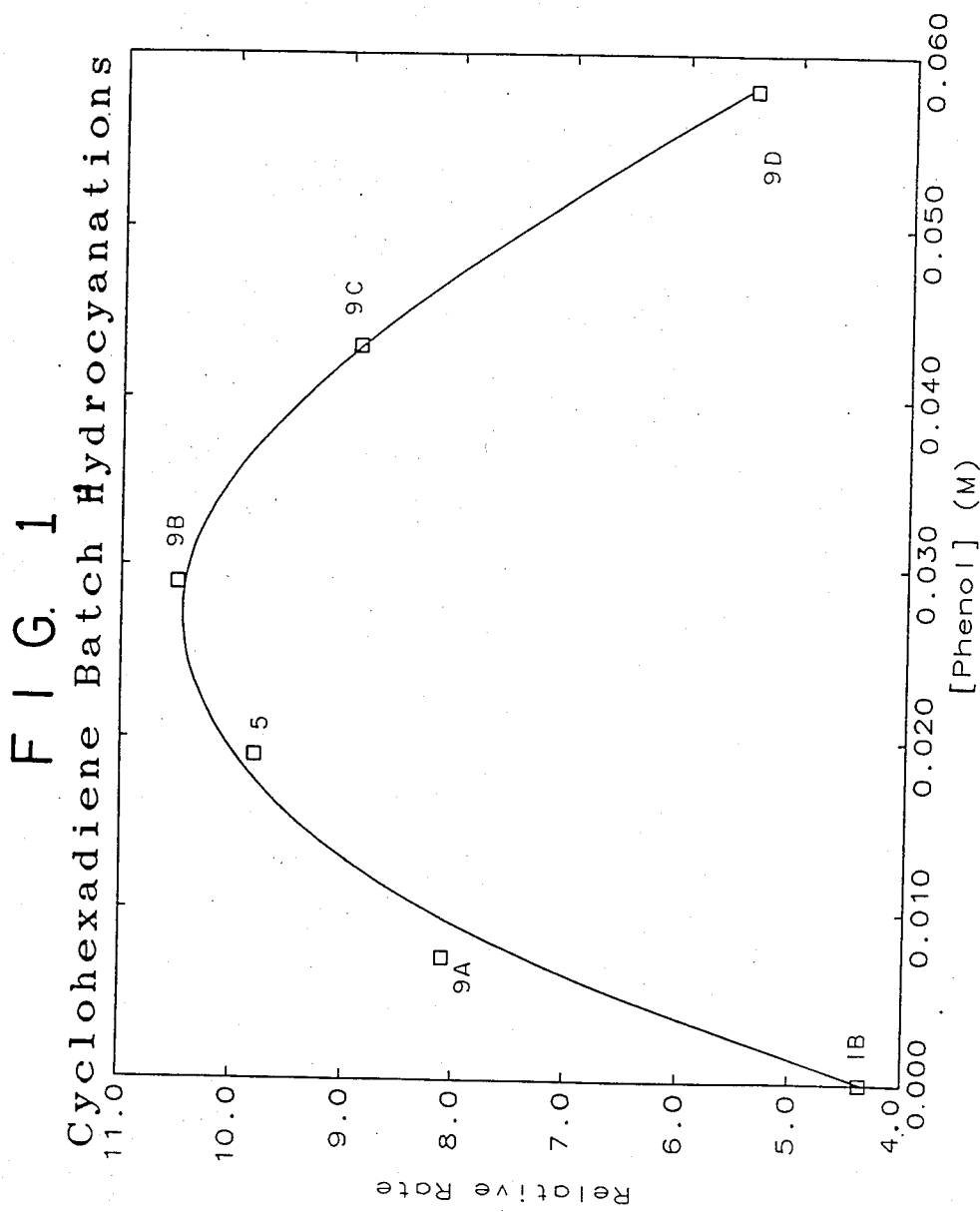
FIG. 1 plots the concentration of phenol against the relative rate of hydrocyanation for cyclohexadiene batch reactions. As the concentration of phenol increases from zero in Comparative Experiment 1b through Examples 9A, 5, 9B, 9C, and 9D, respectively, the relative rate of hydrocyanation increases initially and then decreases with higher concentration levels.
Figure 2:
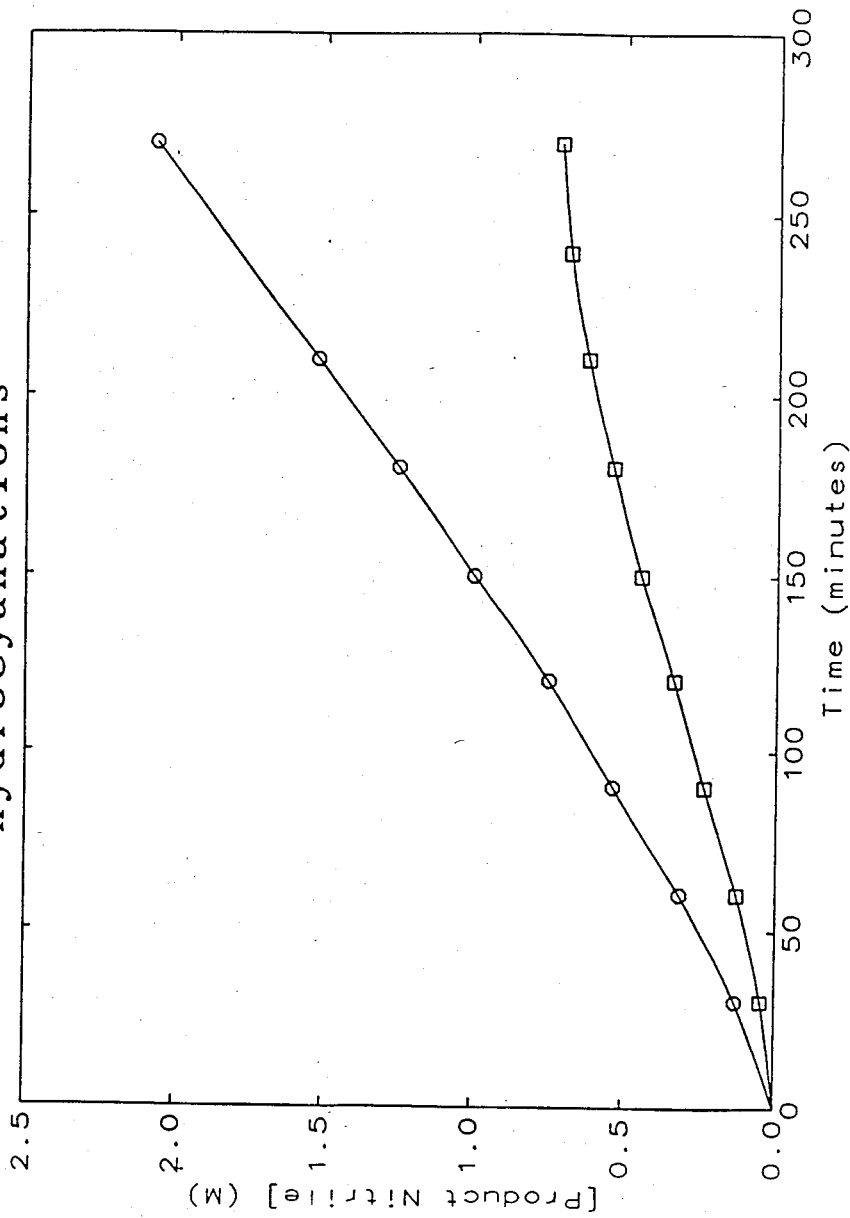
FIG. 2 compares the cyclohexadiene semi-batch hydrocyanation of Example 24 (circles) with that of Comparative Experiment 1g (squares). After 270 minutes, Example 24, with phenol added, produces 2.9 times the amount of nitrile as does Comparative Example 1g, with no phenol added.

In general, the hydrocyanation process is often broken down into two major stages. Thus, with butadiene, for example, the first stage comprises adding hydrogen cyanide to butadiene in the presence of a nickel catalyst, NiL$_4$ wherein L is a phosphorus ligand, to generate pentenenitriles, which are monoenes. In this instance, the second stage consists of pentenenitriles being hydrocyanated by the NiL$_4$ catalyst and a Lewis acid promoter to ultimately yield adiponitrile. These chemical products are important as large-scale, commercial nylon intermediates.

The present invention is an improvement in the first step of the hydrocyanation of polyenes, e.g., dienes such as butadiene, comprising feeding a reactor with the polyene, hydrogen cyanide, a zerovalent nickel catalyst, and, as the improvement, a promotionally effective amount of any acid with a pK$_a$ above about 2 and below about 14, preferably from about 6 to about 12, with phenol and cresols being most preferred.

The starting polyene can be an organic compound selected from the group consisting of any polyene that can isomerize under reaction conditions to a compound containing one or more conjugated double bonds and any polyene containing one or more conjugated double bonds, wherein the polyene is selected from the group consisting of hydrocarbons and hydrocarbons containing groups selected from the group consisting of

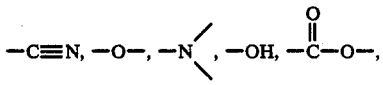

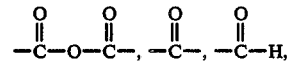

and fluorocarbyls wherein each open bond is connected to a hydrogen or an organic entity and the carbon-carbon double bonds are insulated from any of said groups by at least one carbon, and the organic compound contains from 4 to 22 carbon atoms.

A preferred polyene is a diene of the general formula $$R^6R^7C=C-(CHR)_m-C=CR^8R^9$$

wherein R, R$^6$, R$^7$, R$^8$, and R$^9$ are selected from the group consisting of hydrocarbons and hydrocarbons containing groups selected from the group consisting of

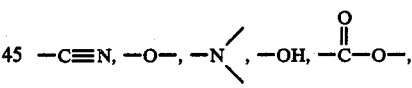

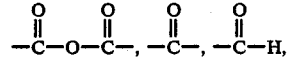

and fluorocarbyls, and m=0 to 20.

The most preferred polyene is selected from the group consisting of butadiene; 1,3-hexadiene; 1,4-hexadiene; 1,5-hexadiene; 1,3-cyclooctadiene; 1,4-cylcooctadiene; 1,5-cyclooctadiene; 1,5,9-cyclododecatriene; cyclopentadiene; dicyclopentadiene; norbornadiene; divinylbenzenes; diisopropenylbenzenes; and divinylcyclobutanes.

The catalysts used in the hydrocyanation process are zerovalent nickel compounds free of carbon monoxide. These nickel compounds may be preformed or prepared in situ and may contain ligands such as alkyl or aryl (either of which can contain up to 18 carbon atoms) phospines, arsines, stibines, phosphites, arsenites, stibites, and mixtures thereof. An especially preferred group of the zerovalent compounds has the general structure

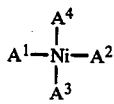

where $A^1$, $A^2$, $A^3$, and $A^4$ are neutral ligands that may be the same or different and that have the formula P(XYZ), wherein X and Y are selected from the class consisting of R and OR and Z has the formula OR, wherein the three R's may be the same or different, and wherein R i selected from the class consisting of alkyl and aryl groups containing up to 18 carbon atoms with aryl being preferred. The R's may be cojoined where possible. An especially preferred class of R's is

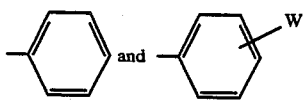

wherein W is selected from the class consisting of Cl, $OCH_3$, and $CH_3$. The neutral ligands of this group are the aryl phospites, e.g., triphenyl phospite, tri-(m- and-/or p-clorophenyl) phosphite, tri-(m- and/or p-methoxyphenyl) phosphite, and tri-(m- and/or p-methylphenyl) phosphite, and mixtures thereof. One or more of $A^1$, $A^2$, $A^3$, and $A^4$ may become dissociated from the nickel during the reaction.

Satisfactory techniques for preparing these nickel compounds may be found in Clark, et al., French Pat. No. 1,297,934, which is stated to be equivalent to Clark et al., U.S. Pat. No. 3,328,443. Other techniques for preparing these catalysts are described in J. Chatt, et al., J. Chem. Soc. (London) 1378–1389 (1960), and in L. S. Meriwether et al., J. Am. Chem. Soc. 81, 4200–4209 (1959). Conventional amounts of zerovalent nickel catalyst are used; however, promotional effects are not as great at very low catalyst levels.

The ligands useful in forming the nickel catalysts may be defined as any atoms or molecules capable of functioning as sigma- and/or pi-bonded partners in one or more coordinate bonds. A description of such ligands is found in F. A. Cotton, et al., Advanced Inorganic Chemistry, John Wiley & Sons (1972), Chapters 21–23.

Given that hydrocyanations of potentially conjugated polyenes take place through the essentially irreversible formation of pi-alkyl nickel complexes from hydrido-nickel complexes and polyolefins, a method of protonating nickel with L$\phi$wry-Bronsted acids that have $pK_a$ values similar to that of hydrogen cyanide can yield nickel species capable of forming these intermediates even in the absence of hydrogen cyanide. Thus, the mechanism of promotion is the conversion of nickel complexes from the resting catalytic state to the active state.

The present invention involves the addition of small amounts of acids to polyene hydrocyanation systems to protonate nickel and, thereby, promote catalysts from a resting state to an active state. The acceleration of diene hydrocyanations is useful, and any polyene that can become a conjugated polyene through a series of 1,3-hydrogen atom shifts, which can be catalyzed by the nickel hydrides present in these reaction mixtures, is a potential starting polyene. Preferred starting polyenes are dienes of the above-specified formula and, in particular, butadiene and related species.

Any acid can be used in the instant process as long as its $pK_a$ value is above about 2 and below about 14, preferably from about 6 to about 12, and as long as the acid-catalyzed alcohol exchange into the ligands employed does not generate an inactive catalyst. Preferred acids include aryl alcohols, such as phenol, cresols, and substituted phenols, which have $pK_a$ values in water of approximately 10. The promotionally effective amount of the acid varies with the polyene selected as well as with reaction conditions. A preferred concentration range is from above 0 to below about 5 M. Above an optimal level, the effectiveness of the catalyst decreases. Preferably, if phenol is used, it is used in low levels because of the cost of removing it from nitrile products.

The hydrocyanation reaction can be carried out by charging a reactor with all of the reactants or, preferably, the reactor is charged with the catalyst or catalyst components, the unsaturated organic compound, and whatever solvent is to be used. The hydrogen cyanide gas is swept over the surface of the reaction mixture or bubbled through the reaction mixture. Another technique is charging the reactor with the catalyst, promoter, hydrogen cyanide, and whatever solvent is to be used and feeding the unsaturated compound slowly to the reaction mixture. Alternatively, reactants can be charged into the reactor and brought to reaction temperature, at which point the hydrogen cyanide is added as a liquid to the mixture, or hydrogen cyanide can be added before heating to reaction temperature. The reaction is run under conventional hydrocyanation conditions for temperature, atmosphere, time, etc.

Preferably, the hydrocyanation is conducted continuously in one or more agitated steps or stages. If a plurality of stages is employed, it is preferred that the stages be in series, with the product from one stage being directed to a subsequent stage. The hydrogen cyanide can be introduced into the first stage or split between stages.

The hydrocyanation reaction can be carried out in the presence or absence of a solvent. If present, the solvent should be liquid at the reation temperature and pressure and inert toward the unsaturated compound and the catalyst. Generally, the solvents are hydrocarbons, such as benzene or xylene, or nitriles, such as acetonitrile or benzonitrile, but preferably a ligand serves as the solvent. As taught herein, aromatic alcohol cannot serve as a solvent because its concentration would then be too great to allow the beneficial aspects of the instant invention to operate.

The preferred methods for acceleration of batch and semi-batch hydrocyanation of various dienes follow. For acceleration of semi-batch hexadiene hydrocyanation, the preferred method is to combine Ni(tri-p-tolylphosphite)$_4$, i.e., Ni(p-TTP)$_4$, catalyst (0.05 M) with excess ligand (0.13 M) in an inert atmosphere with 1,5-hexadiene (5.1 M) and phenol (0.5 M; above 0 M, but below 0.75 M) in a solvent such as toluene. The mixture should be heated at 75° C. and hydrogen cyanide (HCN) added as a part of an otherwise inert vapor or liquid.

The preferred method for acceleration of batch 1,3-cyclohexadiene hydrocyanation is to combine Ni(p-TTP)$_4$ catalyst (0.055 M) with excess ligand (0.68 M) in an inert atmosphere with 1,3-cyclohexadiene (3.8 M) and phenol (0.02 M; above 0 M, but below 0.03 M) in a solvent such as toluene. The mixture should be heated at 75° C. and HCN added as a liquid to the heated solution.

The preferred method for acceleration of semi-batch 1,3-cyclohexadiene hydrocyanation is to combine Ni(p-TTP)$_4$ catalyst (0.055 M) with excess ligand (0.68 M) in an inert atmosphere with 1,3-cyclohexadiene (3.8 M) and phenol (0.04 M; above 0 M, but below 0.35 M) in a solvent such as toluene. The mixture should be heated at 75° C. and HCN added as part of an otherwise inert vapor or liquid.

The preferred method for acceleration of semi-batch hydrocyanation of 1,5-cyclooctadiene is to combine Ni(p-TTP)$_4$ (0.055 M) with excess ligand (0.277 M) in an inert atmosphere with 1,5-cyclooctadiene (4.9 M) and phenol (0.2 M; above 0 M, but below 1 M) in a solvent such as toluene. The mixture should be heated at 75° C. and HCN added as part of an otherwise inert vapor or liquid.

The preferred method for acceleration of semi-batch hydrocyanation of 1,5,9-cyclododecatriene is to combine Ni(p-TTP)$_4$ catalyst (0.055 M) with excess ligand (0.227 M) in an inert atmosphere with 1,5,9-cyclododecatriene (3.3 M) and phenol (0.2 M; above 0 M, but below 1 M) in a solvent such as toluene. The mixture should be heated at 75° C. and HCN added as part of an otherwise inert vapor or liquid.

A similar reaction with butadiene requires facilities capable of operating under pressure and should show a best method similar to the substrates mentioned above.

These preferred methods can operate at catalyst levels from 0.005 to 0.063 M, ligand levels from 0 to 3 M, substrate levels from 1 to 99+%, and solvent levels from 0 to 99+%.

The process of the instant invention is further illustrated by the following examples. In each, the olefins, triphenylphosphite (TPP), tri-p-tolylphosphite (p-TTP), and the aryl alcohols were degassed prior to use; the phosphites were heated under dynamic vacuum at 120° C. prior to use to remove any traces of cresol that might be present. Toluene, when used, was distilled from sodium under argon. All samples were prepared in a Vacuum Atmospheres HE-453 double station drybox equipped with a nitrogen purge system. Drybox freezers were operated at −20° C. Catalyst species, Ni(tri-p-tolylphosphite)$_4$, i.e., Ni(p-TTP)$_4$, and Ni(triphenylphosphite)$_4$, i.e., Ni(TPP)$_4$, were prepared by standard methods. Known concentration solutions of catalyst, ligands, aryl alcohols, and polyolefin were prepared by standard dilution techniques using volumetric glassware.

Samples taken from reactions by microliter syringes were analyzed on a Hewlett Packard HP5890 gas chromatograph equipped with flame ionization and nitrogen/phosphorus (specific) thermionic detectors. Identical 25 meter HP ultra methyl silicones columns were connected to a single split injector, operating at an 150:1 split ratio, and were connected to the two separate detectors. Injections were made using a Hewlett Packard 7673A autosampler, and integrals were recorded using Hewlett Packard HP3392A and HP3390A recording integrators. Data were stored and analyzed on Vax 8650 systems using RS/1 software and an iterative numerical integrator.

The promoting effect of the instant invention is demonstrated in the following examples. The experiments show that the promotional effects are greater at higher catalyst levels, at higher phosphite levels, and at higher olefin concentrations. It is also demonstrated that a variety of aryl alcohols show promotional effects and that different catalyst mixtures also show rate accelerations by added aryl alcohols.

EXAMPLES 1–23

Comparative Experiments 1a–1f & Table 1 Batch Hydrocyanations

In the drybox, a dry 4 mL vial with septum top was charged with 2 mL of a toluene solution of Ni(p-TTP)$_4$ and p-TTP that was 0.043 M in nickel and 0.67 M in free phosphite. 1,3-cyclohexadiene (CHD) was added (1.5 mL) along with acetonitrile (0.5 mL) from a stock solution prepared from 30 mL CHD and 10 mL acetonitrile. Phenol was introduced as a 1.0 M solution (80 μL) in toluene. A stir bar was added and the vial capped. Outside the drybox, the vial was placed in a pre-equilibrated 75° C. oil bath and allowed to equilibrate for 5 minutes while stirring. A total of 80 μL liquid HCN was added from a pre-chilled volumetric syringe. Samples of the material were collected every 5 minutes for 2 hours by μL syringe, and the contents were analyzed by gas chromatography. Toluene was used as the internal standard for measuring concentrations. Table 1 summarizes these results.

TABLE 1

Batch Hydrocyanations

| Example No. or Comp. Exp. No. | [Ni] (M) | [Phosphite] (M) | [CHD] (M) | [ArOH] (M) | Relative Rate | ArOH Type |
|---|---|---|---|---|---|---|
| Examples using 1,3-cyclohexadiene (CHD), Ni(p-TTP)$_4$ catalyst, and p-TTP ligand in toluene at 75° C. (relative rate ±10%; data from pseudo-first order loss of HCN) in 4 mL vials: | | | | | | |
| 1 | 0.021 | 0.32 | 3.78 | 0.019 | 0.93 | phenol |
| 2 | 0.021 | 0.32 | 3.78 | 0.019 | 0.95 | p-methoxyphenol |
| 3 | 0.021 | 0.32 | 3.78 | 0.019 | 0.95 | 2,4,6-trimethylphenol |
| 4 | 0.021 | 0.32 | 3.78 | 0.019 | 0.75 | p-cresol |
| Comp. Exp. 1a | 0.021 | 0.32 | 3.78 | None | 0.80 | — |
| 5 | 0.055 | 0.68 | 3.78 | 0.019 | 9.8 | phenol |
| 6 | 0.055 | 0.68 | 3.78 | 0.019 | 7.0 | p-methoxyphenol |
| 7 | 0.055 | 0.68 | 3.78 | 0.019 | 6.7 | p-cresol |
| 8 | 0.055 | 0.68 | 3.78 | 0.019 | 5.9 | 2,4,6-trimethylphenol |
| 9 | 0.055 | 0.68 | 3.78 | 0.019 | 6.2 | p-fluorophenol |
| 9A | 0.055 | 0.68 | 3.78 | 0.0072 | 8.1 | phenol |
| 9B | 0.055 | 0.68 | 3.78 | 0.029 | 10.5 | phenol |
| 9C | 0.055 | 0.68 | 3.78 | 0.043 | 8.9 | phenol |

TABLE 1-continued

Batch Hydrocyanations

| Example No. or Comp. Exp. No. | [Ni] (M) | [Phosphite] (M) | [CHD] (M) | [ArOH] (M) | Relative Rate | ArOH Type |
|---|---|---|---|---|---|---|
| 9D | 0.055 | 0.68 | 3.78 | 0.058 | 5.4 | phenol |
| Comp. Exp. 1b | 0.055 | 0.68 | 3.78 | None | 4.1 | — |
| 10 | 0.055 | 0.68 | 1.89 | 0.019 | 7.7 | phenol |
| Comp. Exp. 1c | 0.055 | 0.68 | 1.89 | None | 5.0 | — |
| 11 | 0.055 | 1.45 | 1.89 | 0.019 | 4.7 | phenol |
| Comp. Exp. 1d | 0.055 | 1.45 | 1.89 | None | 3.5 | — |
| 12 | 0.036 | 0.45 | 3.78 | 0.019 | 3.8 | phenol |
| 13 | 0.036 | 0.45 | 3.78 | 0.019 | 3.1 | p-methoxyphenol |
| 14 | 0.036 | 0.45 | 3.78 | 0.019 | 3.9 | 2,4,6-trimethylphenol |
| 15 | 0.036 | 0.45 | 3.78 | 0.019 | 3.5 | p-cresol |
| Comp. Exp. 1e | 0.036 | 0.45 | 3.78 | None | 3.3 | — |
| 16 | 0.036 | 0.45 | 3.78 | 0.005 | 4.1 | phenol |
| 17 | 0.036 | 0.45 | 3.78 | 0.010 | 3.7 | phenol |
| 18 | 0.036 | 0.45 | 3.78 | 0.036 | 3.1 | phenol |
| 19 | 0.036 | 0.45 | 3.78 | 0.058 | 3.0 | phenol |
| Examples using mixed (1:1) Ni(TPP)$_4$/Ni(p-TTP)$_4$ catalyst and mixed TTP/p-TTP ligand: | | | | | | |
| 20 | 0.020 | 0.50 | 3.86 | 0.010 | 1.5 | phenol/p-cresol |
| 21 | 0.020 | 0.50 | 3.86 | 0.022 | 1.9 | phenol/p-cresol |
| 22 | 0.020 | 0.50 | 3.86 | 0.044 | 1.7 | phenol/p-cresol |
| 23 | 0.020 | 0.50 | 3.86 | 0.066 | 1.2 | phenol/p-cresol |
| Comp. Exp. 1f | 0.020 | 0.50 | 3.86 | None | 1.3 | — |

EXAMPLES 24-44

Comparative Experiments 1g-1m & Table 2 Semi-batch Hydrocyanations

In a drybox, a dry 25 mL 3-necked, round bottom flask was charged with a stirring bar, 5 mL of CHD, and 5 mL of a solution containing Ni(TPP)$_4$ and Ni(p-TTP)$_4$ (in a 1:1 ratio; total [Ni]=0.044 M) as well as TPP and p-TTP (in a 1:1 ratio; total [P]=1.28 M) in toluene and 75 μL of 6.0 M phenol solution in toluene. The solution was heated at 75° C. as HCN vapor was blown into the reactor in an argon current at 2 mL HCN gas/minute. Samples were collected every 10 minutes and were analyzed by gas chromatography. An identical reaction was run in the absence of phenol (Comparative Experiment 1j). The reaction containing phenol generated cyclohexenenitriles at a rate three times faster than the control experiment. In addition, HCN buildup was noted when no cresol was present, whereas, in Example 46, HCN was consumed as fast as added.

Greatest promotional effectiveness appears to occur when the concentrations of other acids in the system, e.g., HCN, are lowest. Initially, the phenol accounts for only 5% of the acid in the system whereas, when 90% of the HCN has been consumed, the phenol accounts for 33% of the acid in the system (at 0.025 M phenol levels). In order to examine this effect under HCN-starved reation conditions, these semi-batch reactions were conducted. Table 2 summarizes these results.

TABLE 2

Semi-Batch Hydrocyanations

| Example No. or comp. Exp. No. | [Ni] (M) | [Phosphite] (M) | [ArOH] (M) | Relative Rate | ArOH Type |
|---|---|---|---|---|---|
| 1,3-cyclohexadiene (CHD) semi-batch reactions: [CHD] = 5.24 M; catalyst = Ni(p-TTP)$_4$; T = 75° C.; relative rate corresponds to amount of nitrile formed after 270 minutes. | | | | | |
| Comp. Exp. 1g | 0.022 | 0.64 | None | 1.0 | — |
| 24 | 0.022 | 0.64 | 0.045 | 2.9 | phenol |
| 1,5-cyclooctadiene (COD) semi-batch reactions: [COD] = 4.9 M; catalyst = Ni(p-TTP)$_4$; T = 75°; relative rate corresponds to amount of nitrile formed after 60 minutes. | | | | | |
| Comp. Exp. 1h | 0.062 | 0.227 | None | 1.0 | — |
| 25 | 0.062 | 0.227 | 0.03 | 2.2 | phenol |
| 1,5,9-cyclododecatriene (CDDT) semi-batch reactions: [CDDT] = 3.3 M; catalyst = Ni(p-TTP)$_4$; T = 75° C.; relative rate corresponds to amount of nitrile formed after 30 minutes. | | | | | |
| Comp. Exp. 1i | 0.055 | 0.227 | None | 1.0 | — |
| 26 | 0.055 | 0.277 | 0.03 | 2.0 | phenol |
| 1,5-hexadiene (HD) semi-batch reactions: [HD] = 5.1 M; catalyst = Ni(p-TTP)$_4$; T = 50° C.; relative rate corresponds to amount of nitrile formed after 60 minutes. | | | | | |
| Comp. Exp. 1j | 0.055 | 0.227 | None | 1.0 | — |
| 27 | 0.055 | 0.227 | 0.005 | 1.3 | phenol |
| 1,5-hexadiene (HD) semi-batch reactions: [HD] = 3.88 M; catalyst = Ni(p-TTP)$_4$; T = 50° C.; relative rate corresponds to amount of nitrile formed after 90 minutes. | | | | | |
| Comp. Exp. 1k | 0.030 | 0.13 | None | 1.0 | — |
| 28 | 0.030 | 0.13 | 0.20 | 3.2 | phenol |
| 29 | 0.030 | 0.13 | 0.71 | 3.1 | phenol |
| 30 | 0.030 | 0.13 | 1.97 | 2.9 | phenol |
| 31 | 0.030 | 0.13 | 3.59 | 1.8 | phenol |
| 1,5 (HD) semi-batch reactions: [HD] = 5.1 M; catalyst = Ni(p-TTP)$_4$; T = 50° C.; relative rate corresponds to amount of nitrile formed after 90 minutes. | | | | | |
| Comp. Exp. 1l | 0.055 | 0.227 | None | 1.0 | — |
| 32 | 0.055 | 0.227 | 0.025 | 2.6 | phenol |
| 33 | 0.055 | 0.227 | 0.075 | 4.6 | phenol |
| 34 | 0.055 | 0.227 | 0.150 | 5.4 | phenol |
| 35 | 0.055 | 0.227 | 0.30 | 8.8 | phenol |
| 36 | 0.055 | 0.227 | 0.50 | 9.8 | phenol |
| 1,3-cyclohexadiene (CHD) semi-batch reactions: [CHD] = 4.4 M; catalyst = Ni(p-TTP)$_4$; T = 50° C.; relative rate corresponds to amount of nitrile formed after 90 minutes. | | | | | |
| Comp. Exp. 1m | 0.036 | 0.15 | None | 1.0 | — |
| 37 | 0.036 | 0.15 | 0.021 | 1.1 | phenol |
| 38 | 0.036 | 0.15 | 0.043 | 1.3 | phenol |
| 39 | 0.036 | 0.15 | 0.085 | 1.3 | phenol |

TABLE 2-continued

Semi-Batch Hydrocyanations

| Example No. or comp. Exp. No. | [Ni] (M) | [Phosphite] (M) | [ArOH] (M) | Relative Rate | ArOH Type |
|---|---|---|---|---|---|
| 40 | 0.036 | 0.15 | 0.180 | 1.3 | phenol |
| 41 | 0.036 | 0.15 | 0.350 | 1.0 | phenol |
| 42 | 0.036 | 0.15 | 0.710 | 0.9 | phenol |
| 43 | 0.036 | 0.15 | 1.420 | 0.6 | phenol |
| 44 | 0.036 | 0.15 | 3.540 | 0.41 | phenol |

What is claimed is:

1. An improved process for hydrocyanation of a polyene selected from the group consisting of any polyene that can isomerize under reaction conditions to a compound containing one or more conjugated double bonds and any polyene containing one or more conjugated double bonds with hydrogen cyanide in the presence of a zerovalent nickel catalyst under liquid phase conditions comprising conducting the process with a promotionally effective amount from above aobut 0 to below about 5 M of any acid with a $pK_a$ above about 2 and below about 14 in the presence or absence of a solvent.

2. A process according to claim 1 wherein a promotionally effective amount from above about 0 to below about 5 M of any acid with a $pK_a$ from about 6 to about 12 is used.

3. A process according to claim 1 wherein the acid is an aryl alcohol of the structure

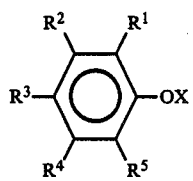

wherein
X is any isotope of hydrogen, and
$R^1$, $R^2$, $R^3$, $R^4$, and $R^5$ are selected from the group consisting of hydrogen, hydrocarbyls, and hydrocarbyls containing groups selected from the group consisting of

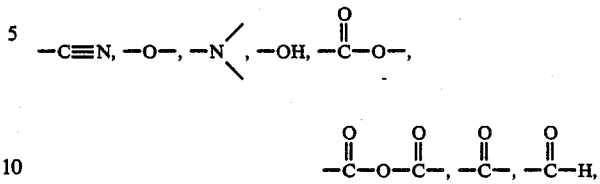

halides, and fluorocarbyls.

4. A process according to claim 3 wherein the aryl alcohol is selected from the group consisting of phenol and cresols.

5. A process acording to claim 1, 2, 3, or 4 wherein the polyene is selected from the group consisting of butadiene; 1,3-hexadiene; 1,4-hexadiene; 1,5-hexadiene; 1,3-cyolooctadiene; 1,4-cyclcooctadiene; 1,5-cyclooctadiene; 1,5,9-cyclododecatriene; cyclopentadiene; dicyclopentadiene; norbornadiene; divinylbenzenes; diisopropenylbenzenes; and ivinylcyclobutanes.

6. A process according to claim 1, 2, 3, or 4 wherein the polyene is a diene of the formula

wherein R, $R^6$, $R^7$, $R^8$, and $R^9$ are selected from the group consisting of hydrocarbons and hydrocarbons containing groups selected from the group consisting of

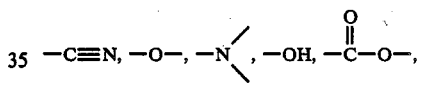

and fluorocarbyls, and m=0 to 20.

UNITED STATES PATENT AND TRADEMARK OFFICE
CERTIFICATE OF CORRECTION

PATENT NO. : 4,810,815
DATED : March 7, 1989
INVENTOR(S) : Henry Edward Bryndza

It is certified that error appears in the above-identified patent and that said Letters Patent is hereby corrected as shown below:

Column 12, line 22, the word "ivinylcyclobutanes" should read --divinylcyclobutanes--.

Signed and Sealed this

Fifteenth Day of August, 1989

Attest:

DONALD J. QUIGG

Attesting Officer

Commissioner of Patents and Trademarks